United States Patent [19]  
Heil et al.

[11] 4,089,115  
[45] May 16, 1978

[54] SPRING GRIP CHUCK ASSEMBLY FOR DENTAL HANDPIECES

[75] Inventors: Donald J. Heil, Lake Villa; Boubene M. Jaremus, Barrington, both of Ill.

[73] Assignee: American Hospital Supply Corporation, Evanston, Ill.

[21] Appl. No.: 742,551

[22] Filed: Nov. 17, 1976

[51] Int. Cl.² ............................................. A61C 1/10
[52] U.S. Cl. ................................. 32/27; 279/1 SG; 279/20
[58] Field of Search ................ 32/26, 27; 279/1 SG, 279/20, 23

[56] References Cited  
U.S. PATENT DOCUMENTS 2,263,808  11/1941  Hutchinson ............................. 32/27
3,376,084  4/1968  McKee ..................................... 32/27

Primary Examiner—Robert Peshock  
Attorney, Agent, or Firm—Tilton, Fallon, Lungmus & Chestnut

[57] ABSTRACT

A dental handpiece having a rotor housing with a chamber, a rotor within the chamber, and an improved spring grip chuck. The chamber has upper and lower openings coaxial therewith, the rotor has a bore aligned with the openings, and the chuck is received within the bore. The chuck is fixed to the bore and has a plurality of tapered spring jaws at its upper end which normally slope inwardly for frictionally contacting and holding a dental bur. The upper end of the bore is provided with a pusher nut which is accessible by means of a suitable wrench through the upper opening in the housing and which is adjustable for engaging and forcing open the jaws to permit removal and replacement of the bur.

13 Claims, 4 Drawing Figures

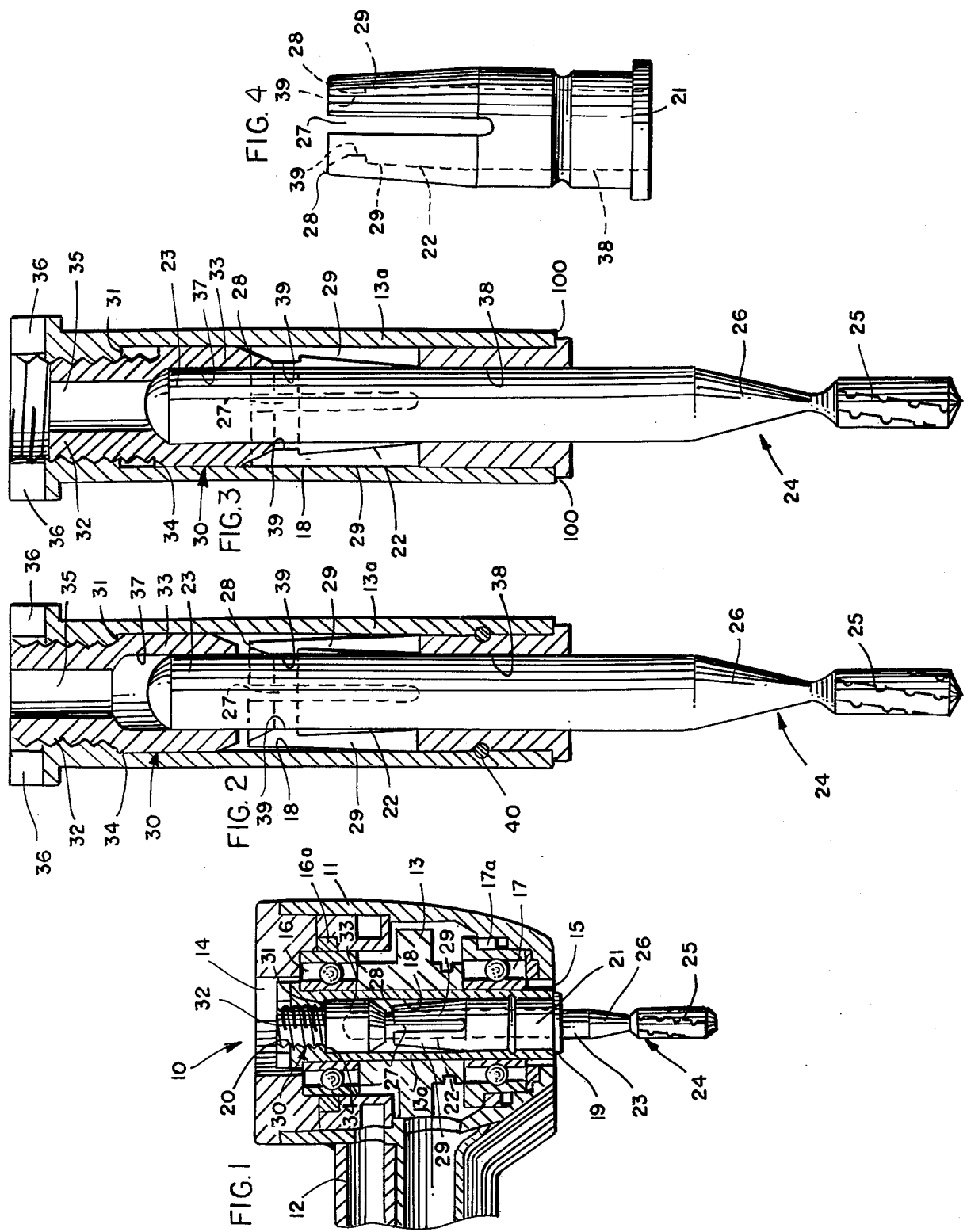

SPRING GRIP CHUCK ASSEMBLY FOR DENTAL HANDPIECES

BACKGROUND

The chucks commonly used in high speed dental handpieces for releasably holding dental burs in place have chucking actions that can be generally categorized as falling within one of two groups. The first groups includes the wrench operated pull-to-tighten and push-to-tighten types of chucks. The second group includes the spring grip chuck. While efforts have been made to develop a fully satisfactory chuck which overcomes certain disadvantages that have come to be associated with chucks of these types, such efforts have not been entirely satisfactory.

Both wrench operated pull-to-tighten and push-to-tighten chucks tend to undergo bur "walkout" or ejection during conditions of extremely heavy cutting particularly in tenacious types of materials such as gold alloys and some silver amalgams under which the cutting dynamics are very severe. Test work has shown such axial walkout may occur even without any accompanying torsional slippage of the bur. Furthermore, such wrench operated chucks occasionally present a further problem, that of the chuck unscrewing from the rotor and possibly releasing during handpiece operation.

A variation of the push-to-tighten chuck is a double ended type with a separate nut. Advantages in elimination of bur walkout can generally be expected with this type of chuck but definite disadvantages include the nut loosening during cutting with the possible result being that the chuck, bur, or tightening nut will unscrew and either jam the handpiece or even possibly allow the loose pieces to fly through the air with injurious velocity.

The spring grip type chucks heretofore known also have the advantage of generally overcoming the problem of bur walkout or ejection but are commonly associated with other troublesome disadvantages. In the use of a spring grip chuck, the bur is normally removed by utilizing a small diameter push rod which the operator must direct with a force strong enough to overcome the spring and frictional forces. Conversely, in order to insert the bur into this type of chuck, the bur must generally be placed against a soft brass or plastic slug so it can be pushed into place without damage to the bur surface against which the slug is pushed. Major disadvantages of spring grip chucks have resided in the fact that it is often difficult and dangerous for an operator to apply sufficient force to overcome the springs for bur insertion and removal without damaging the bur, the handpiece, or both.

SUMMARY

The present invention is primarily concerned with a construction which overcomes all of the aforementioned defects and disadvantages of the prior art and at the same time achieves many additional advantages. The construction more specifically concerns a dental handpiece having an improved spring grip chuck that effectively prevents bur walkout and can be wrench operated without any parts that might become loose and possibly fly out during a cutting operation. The chuck of the present invention is relatively simple and durable in construction in addition to achieving such noted advantages.

The improved spring grip chuck is characteristically used with a dental handpeice of the type having a rotor housing with a chamber and with upper and lower opening coaxial therewith and a rotor within the chamber having a bore aligned with the openings. The chuck is received within the bore having a plurality of jaws at its upper ends to provide an inwardly directed spring force. The lower portion of the chuck is fixed relative to the bore and the jaws are defined by longitudinal slots which extend downward from the upper end of the chuck terminating adjacent to or slightly below the tapered portions of the jaws. A control member is disposed at the upper end of the bore, and is accessible through the upper opening in the housing, for forcing open the jaws to permit bur ingress and egress.

The control member for opening the jaws takes the form of a pusher nut which is threadedly engaged for axial adjustment within the bore. The outer surface of the pusher nut is beveled inwardly at its lower end and the corresponding inner surfaces of the jaws are beveled outwardly at their upper ends. The bore preferably includes stop means near its upper end to limit upward movemnt of the pusher nut.

The pusher nut is operable between a fully raised position against the stop means and a fully lowered position in which the beveled outer surface of the pusher nut is in mating engagement with the beveled inner surfaces of the jaws and the outer surfaces of the jaws are in contact with the bore. The opening or passage of the chuck below the jaw serves as a pilot to guide a bur into the handpiece, thus giving good bur concentricity; and the underside of the pusher nut is recessed to accept the bur, serves as a pilot for slidably receiving and centering the upper end of the bur, and the end of the pilot provides an axial bur positioning stop. The jaws are positioned between these upper and lower pilots and include inwardly projecting contact portions near their upper ends to engage and frictionally hold the bur securely in place within the handpiece.

It is therefore an object of the present invention to provide an improved wrench operated spring grip chuck wherein the chuck is fixed to the bore and has jaws located at its upper end for use in combination with a dental handpiece. Another objective of this invention is to provide a chuck that cannot be damaged by overtightening because tightening action translates the pusher nut away from the jaws until the threads bottom out thus there is no contact with the chuck jaws. The provision of the structure and the realization of the advantages to be derived therefrom constitute additional important objects of this invention. Other objects of the present invention can be appreciated from the details of construction and operation set forth in the accompanying specificatiions, claims and drawings.

DRAWINGS

The invention is described in conjunction with the accompanying drawings in which:

FIG. 1 is a sectional view of a dental handpiece utilizing an improved chuck in accordance with the present invention;

FIG. 2 is an enlarged sectional view of the spring grip chuck and a pusher nut showing their relationship with the pusher nut in a fully raised position;

FIG. 3 is an enlarged sectional view of the spring grip chuck and a pusher nut showing their relationship with the pusher nut in a fully lowered position; and FIG. 4 is a side elevation of the spring grip chuck in accordance with the present invention.

DESCRIPTION

In the illustration given and with reference first to FIG. 1, the numeral 10 generally designates a dental handpiece of the air-driven type. The handpiece 10 has an outer housing 1 which includes a neck portion 12. Within the chamber of the housing 11 is a rotor 13 adapted to be driven by air supplied through the handle (not shown) and neck 12.

The housing 11 also includes upper and lower openings 14 and 15 formed therein. The openings 14 and 15 are axially aligned with the rotor 13 being supported for rotation by upper and lower bearing assemblies 16 and 17. Although of little importance for purposes of understanding the invention, resilient rings 16a and 17a are interposed respectively between the bearings 16 and 17 and the walls of the housing 11 for purposes of reducing noise levels during handpiece operation.

The rotor 13 includes a bur tube 13a which extends substantially between openings 14 and 15 having a central bore 18 axially aligned with those openings. It will be observed that the bore 18 has a lower end 19 adjacent the lower opening 15 in the housing 11. At the upper end 20 of the bore 18 adjacent the upper opening 14 in the housing 11, the bur tube 13a has internal threads for a purpose to be described in detail below. The lower end 19 of the bore 18 receives an improved spring grip chuck 21 which is fixed to the bur tube 13a.

The chuck 21 extends upwardly from the lower opening 15 in the housing 11 preferably slightly greater than halfway through the bore 18. The bore 22 is provided in the chuck 21 which is adapted to receive the shank 23 of a standard dental bur 24. The standard dental bur 24 can more completely be defined as having a shank 23 and a cutting head 25 joined together by a transitional conic region 26.

The chuck 21 includes longitudinal slots 27 (as shown in FIG. 4) which extend downwardly from the upper end 28 of the chuck 21 to define a plurality of circumferentially spaced spring jaws 29 characterized by radial elasticity. The jaws 29 grip the shank 23 of the bur 24 when it is in place within the bore 22 of the chuck 21. The spring jaws 29 not only taper upwardly but (as shown most clearly in FIGS. 2 and 4) such jaws normally slope inwardly and upwardly. When untensioned, the jaws 29 have their inner surfaces inclined inwardly and upwardly to define an opening at their tips at the end 28 of the chuck 21, which is substantially smaller than the cross-sectional dimensions of the dental bur 24, and the outer surfaces of the jaws 29 angle inwardly out of contact with the cylindrical surface of the bore 18. When the bur 24 is positioned (as shown in FIG. 2), the spring tension of the jaws 29 securely hold the bur in place.

Control means 30 is provided so as to be accessible through the upper opening 14 in the housing 11 for opening the jaws 29. In the illustration given, means 30 comprises a pusher nut which is threadedly engaged for axial movement within the bore 18 at its upper end 20. The bore 18 preferably includes stop means in the form of a shoulder or annular offset 31 provided immediately below the upper end 20 to restrict upward movement of the pusher nut 30.

The pusher nut 30 includes an upper portion 32 and a lower portion 33. The upper portion 32 is provided with external threads which mate with the internal threads at the upper end 20 of the bore 18. The lower portion 33 has a smooth outer surface which engages the smooth inner surface of the bore 18 below the upper end 20. The lower portion 33 and the upper portion 32 are radially offset with respect to one another (as shown in FIGS. 2 and 3) to define a shoulder 34 therebetween.

A non-circular socket 35 is provided in the upper portion 32 of the pusher nut 30 to receive a suitable wrench element (not shown) for adjusting the pusher nut 30 axially downwardly and upwardly with respect to the bore 18. In the illustration given, the socket 35 may be of any suitable noncircular cross-sectional configuration although a hexagonal or square cross-sectional configuration is deemed particularly effective. It will be observed that notches 36 are formed in the upper end of the bur tube 13a for the purpose of holding the rotor 13 stationary relative to the nut 30 (or of rotating the rotor 13 relative to the stationary nut 30) during adjustment of the pusher nut 30.

The lower portion 33 of the pusher nut 30 includes a cylindrical bore 37 which can, as shown, communicate with non-cylindrical bore 35 in the upper portion 32. The inner surface of the bore 37 serves as a pilot for slidably receiving and centering the upper end of the bur 24. Similarly, a cylindrical passage 38 through the lower portion of the chuck 21 slidably receives and directs the bur 24. The handpiece 10 therefore utilizes two pilots to guide the bur 24 with one being provided above and one being provided below the jaws 29. The cylindrical passage 38 of the chuck 21 and the bore 37 of the pusher nut 30 must, of course, be in axial alignment and have diameters only slightly larger than the shank diameter of the bur 24.

The outer surface of the lower portion 33 of the pusher nut 30 is beveled inwardly at its lower end and the inner surfaces of the jaws 29 are beveled outwardly at their upper ends. The beveled surfaces are provided in a manner that permits them to matingly engage so that the pusher nut 30 can cam open the jaws 29. In order for the bur 24 to be removed from or inserted in the chuck 21, the jaws 29 must, of course, be opened and the pusher nut 30 accomplishes this in a manner that will become apparent below.

Inwardly projecting contact portions 39 are provided near the upper ends of the jaws 29 but immediately below the beveled inner surfaces thereof to engage and hold the bur 24 within the handpiece 10. The contacts 39 form an interrrupted annular ring and the spring force of the jaws 29 is applied through the ring to the shank 23 of the bur 24. The bur 24 is firmly held in position by the contacts 39 since any movement in the axially downward direction is resisted by the strong frictional force on the shank 23 caused by the upward and inward taper of the jaws 29. The chuck 21 itself cannot move with respect to the bore 18 since its lower portion is fixed within the bore 18 by means of a snap ring 40 (as shown in FIG. 2) or, alternatively, by means of a laser weld 100 (as shown in FIG. 3). The improved spring grip chuck 21 of the present invention therefore has no parts to become loose and fly out during a cutting operation and effectively resists any tendency of bur walkout or ejection.

The important advantages to be derived from the improved spring grip chuck 21 of the present invention described hereinabove can more fully be understood and appreciated in connection with a description of the use of the chuck 21 in the handpiece 10. The pusher nut 30 is backed off away from the chuck 21 (as shown in FIG. 2) with the shoulder 34 of the pusher nut 30 in contact with the annular offset 31 during operation of the handpiece 10. The jaws 29 provide a substantial inwardly directed spring force through the contacts 39 near the mid-point of the shank 23 to retain the bur 24 firmly in position within the chuck 21. The pusher nut 30 can later be advanced axially downwardly within the bur tube 13a (as shown in FIG. 3) until the beveled outer surface of the pusher nut 30 matingly engages the beveled inner surfaces of the jaws 29 to force them open. The opening of the jaws 29 gradually occurs because the lower portion 33 of the pusher nut 30 exerts greater and greater pressure on the jaws 29 until the outer surface of the jaws 29 have gradually been forced into contact with the bore 18. The bur 24 can then easily be removed from the chuck 21 with the bore 37 and the passage 38 serving as pilots since the jaws 29 are no longer in contact with the shank 23.

With the pusher nut 30 in its downward position, the jaws 29 are in a fully open position and the chuck 21 can again later easily receive the bur 24. The passage 38 and the bore 37 serve as pilots to slidably receive and guide the bur 24 into a centered position to provide bur concentricity. The bur 24 is urged upwardly through the passage 38 and the bore 37 until the upper end of the shank 23 (as shown in FIG. 3) is in contact with the upper end of the bore 37 which serves as an axial bur positioning stop. The pusher nut 30 is then advanced axially upwardly within the bur tube 13a either moving relative to the bur 24 or causing the bur 24 to be drawn upwardly as well depending upon the respective diameters of the shank 23 and the bore 37. In any event, the jaws 29 gradually resume their partially closed but still tensioned positions of inward angulation gripping the shank 23 to prevent further axial movement of the bur 24. The pusher nut 30 is further backed away from the chuck 21 (as shown in FIG. 2) until the shoulder 34 of the pusher nut 30 is in contact with the annular offset 31. The chuck 21 therefore cannot be damaged by overtightening because tightening action translates the pusher nut 30 away from and out of contact with the jaws 29. With the pusher nut 30 in the fully upward position and the jaws 29 providing a substantial inwardly directed spring force through the contacts 39 near the mid-point of the shank 23, the bur 24 is firmly held in position within the chuck 21 and the handpiece 10 is again ready for operation.

It should now be clear that the pusher nut 30 is operable between a fully raised position with the shoulder 34 in engagement with the annular offset 31 and a lowered position with the beveled outer surface of the pusher nut 30 in mating engagement with the beveled inner surfaces of the jaws 29. The outer surfaces of the jaws 29 will be in contact with, or in close proximity to, the bore 18 when the pusher nut 30 is in a fully lowered position and the interrupted annular surface defined by the contacts 39 will have a diameter greater than the diameter of the passage 38 or of the bore 37. When the pusher nut 30 is in a fully raised position, the outer surfaces of the jaws 29 slope inwardly and upwardly away from the bore 18, and the interrupted annular surface defined by the contacts 39 have a diameter (at least in the absence of bur 24) less than the diameter of the passage 38 or of the bore 37. As a result, the jaws 29 permit free bur ingress and egress when the pusher nut 30 is in the fully lowered position whereas when the pusher nut 30 is in the fully raised position, the jaws tightly and securely clamp the bur in place.

While in the foregoing specification a detailed description of the invention has been set forth for the purpose of illustration, variations of the details herein given may be made by those skilled in the art without departing from the spirit and scope of the invention.

We claim:

1. An improved dental handpiece of the type having a rotor housing with a chamber and with upper and lower openings coaxial therewith, a rotor within said chamber having a bore aligned with said openings, and a tubular chuck received in said bore, wherein the improvement comprises said chuck being fixed to said rotor within said bore and having a plurality of upwardly projecting circumferentially spaced spring jaws, said jaws normally sloping upwardly and inwardly into partially closed positions for firmly gripping a dental bur therebetween and being capable of being flexed outwardly into open positions for releasing such bur, and control means provided at the upper end of said bore and accessible through said upper opening in said housing for engaging said jaws and flexing same into said open positions.

2. The improved structure of claim 1 in which said control means comprises a pusher nut which is threadedly engaged within said bore.

3. The improved structure of claim 2 in which the outer surface of the lower portion of said pusher nut is beveled inwardly at its lowermost end.

4. The improved structure of claim 3 in which the inner surfaces of the upper portion of said jaws are beveled outwardly at their uppermost ends.

5. The improved structure of claim 4 in which said bore includes stop means near its upper end to limit upward movement of said pusher nut thereby preventing overtightening of said chuck that could cause damage to said jaws.

6. The improved structure of claim 5 in which said pusher nut is operable between a fully raised position against said stop means and a fully lowered position in which said beveled outer surface of said pusher nut is in mating engagement with said beveled inner surfaces of said jaws and the outer surfaces of said jaws are in contact with said bore.

7. The improved structure of claim 2 in which said chuck includes a cylindrical pilot passage below said jaws for slidably receiving and guiding a bur into said handpiece to provide good concentricity of the bur.

8. The improved structure of claim 7 in which said pusher nut is provided with a pilot recess at its lower end for slidably receiving and centering the end of a dental bur with the upper end of said recess acting as an axial positioning stop for the bur.

9. The improved structure of claim 2 in which said jaws include inwardly projecting contact portions near their upper ends thereof for frictionally engaging and holding a bur in said handpiece.

10. The improved structure of claim 2 in which the lower portion of said chuck is fixed to said bore by means of a snap ring.

11. The improved structure of claim 2 in which the lower portion of said chuch is fixed to said bore by means of a weld.

12. The improved structure of claim 2 in which said jaws are defined by longitudinal slots extending downward from the upper end of said chuck to provide radial elasticity to said jaws.

13. The improved structure of claim 1 in which a dental bur is disposed within said handpiece.

* * * * *